(12) United States Patent
Hoffman

(10) Patent No.: US 6,474,990 B2
(45) Date of Patent: Nov. 5, 2002

(54) DENTAL SALIVA EJECTOR TUBE ASSEMBLY

(76) Inventor: Elliott S. Hoffman, 5001 Desert Jewel Dr., Paradise Valley, AZ (US) 85253

( * ) Notice: Subject to any disclaimer, the term of this patent is extended or adjusted under 35 U.S.C. 154(b) by 0 days.

(21) Appl. No.: 09/841,354

(22) Filed: Apr. 24, 2001

(65) Prior Publication Data

US 2001/0024778 A1 Sep. 27, 2001

Related U.S. Application Data

(63) Continuation-in-part of application No. 09/344,027, filed on Jun. 25, 1999, now Pat. No. 6,220,859, which is a continuation of application No. 09/014,838, filed on Jan. 28, 1998, now Pat. No. 5,931,671.

(51) Int. Cl.[7] .................................................. A61C 17/06
(52) U.S. Cl. ........................... 433/91; 433/126; 604/283
(58) Field of Search ............................ 433/91, 93, 94, 433/95, 96, 126, 127, 129; 604/103, 283; 285/311, 312, 320

(56) References Cited

U.S. PATENT DOCUMENTS

| | | | |
|---|---|---|---|
| 2,873,528 A | 2/1959 | Thompson | 433/96 |
| 3,453,735 A | 7/1969 | Burt | 433/96 |
| 3,874,712 A | 4/1975 | Watson | 285/236 |
| 4,083,115 A | 4/1978 | McKelvey | 433/93 |
| 4,204,328 A | 5/1980 | Kutner | 433/29 |
| 4,405,163 A | 9/1983 | Voges et al. | 285/305 |
| 4,436,125 A | 3/1984 | Blenkush | 141/330 |
| 4,822,278 A | 4/1989 | Oliva et al. | 433/91 |
| 4,850,984 A | 7/1989 | Harris | 604/326 |
| 4,966,551 A | 10/1990 | Betush | 433/95 |
| 4,969,879 A | 11/1990 | Lichte | 604/283 |
| 5,267,984 A | 12/1993 | Doherty | 604/283 |
| 5,295,826 A | 3/1994 | Yandell et al. | 433/31 |
| 5,299,838 A * | 4/1994 | Yang | 285/88 |
| 5,651,771 A | 7/1997 | Tangherlini et al. | 604/158 |
| 5,931,671 A | 8/1999 | Hoffman | 433/91 |
| 6,220,859 B1 | 4/2001 | Hoffman | 433/91 |

OTHER PUBLICATIONS

Jan. 1997 Darby Dental Supply Co. Inc. Catalog Excerpt; p. 298.

* cited by examiner

Primary Examiner—John J. Wilson
(74) Attorney, Agent, or Firm—Cahill, Sutton & Thomas, P.L.C.

(57) ABSTRACT

A socket for removably receiving an end of a dental saliva ejector tube includes a central body having a first end forming a port for being coupled to a vacuum hose. The central body includes a passage extending therethrough from the first end toward a second opposing and that includes an enlarged bore forming a socket for receiving the end of the dental saliva ejector tube. A lever, slide member, or other movable retaining member is movably secured to the central body for selectively engaging, or moving away from, the sidewall of the ejector tube. The movable retaining member includes a sharpened tip for lightly digging into the sidewall of the ejector tube. A biasing spring may be provided for urging the retaining member into engagement with the sidewall of the ejector tube. A user may depress or otherwise actuate the retaining member to move it away from the ejector tube to insert or remove the ejector tube from the socket.

9 Claims, 4 Drawing Sheets

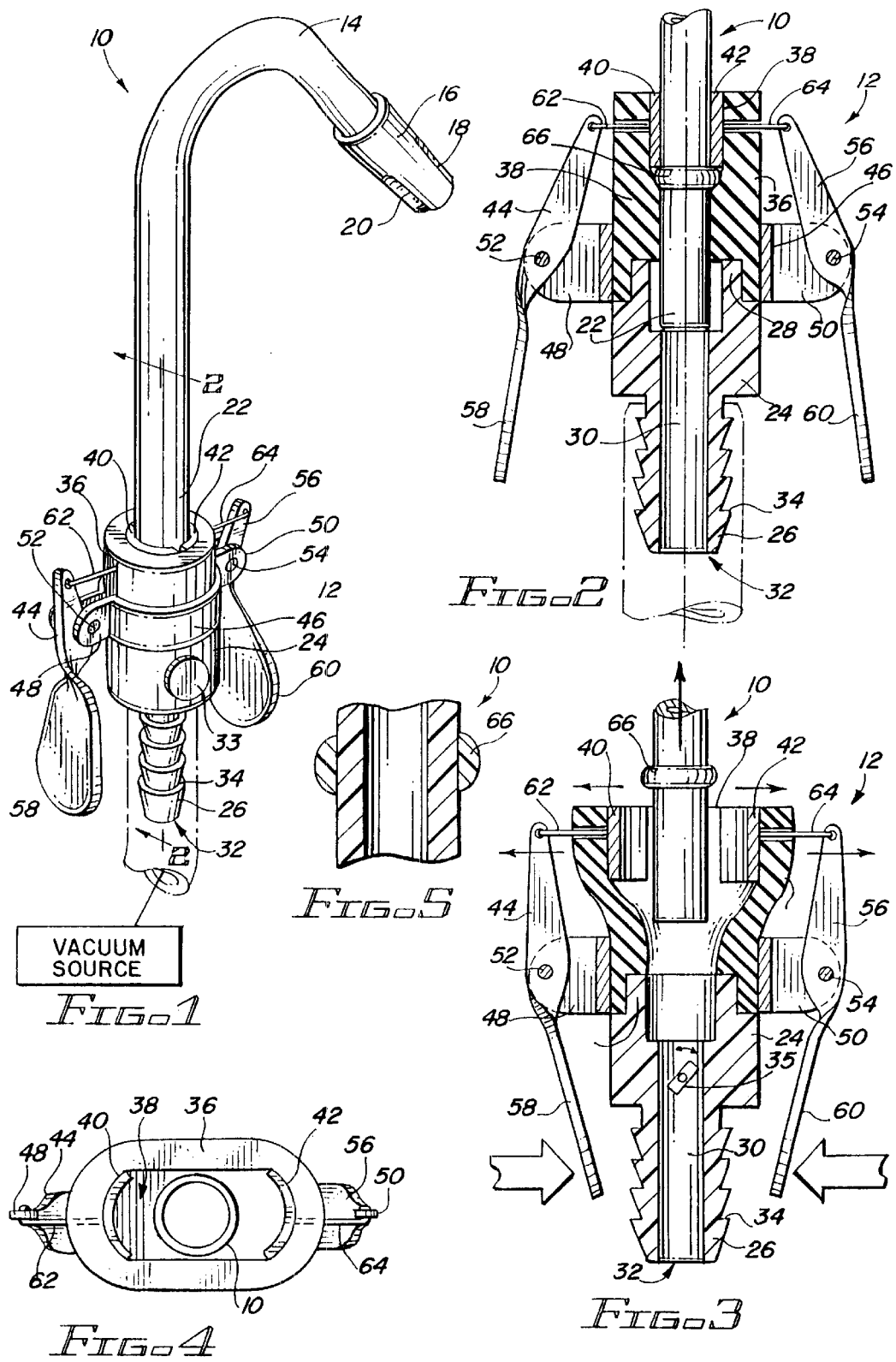

DENTAL SALIVA EJECTOR TUBE ASSEMBLY

CROSS-REFERENCE TO RELATED PATENT APPLICATIONS

The present application is a continuation-in-part of patent application Ser. No. 09/344,027, filed on Jun. 25, 1999, now U.S. Pat. No. 6,220,859, which is a continuation of parent patent application Ser. No. 09/014,838, filed on Jan. 28, 1998, now U.S. Pat. No. 5,931,671, and the benefit of the filing dates of such earlier-filed applications under 35 U.S.C. §120 is hereby claimed.

BACKGROUND OF THE INVENTION

1. Field of the Invention

The present invention relates to dental saliva ejector tubes, and more particularly, to vacuum sockets for releasably receiving dental saliva ejector tubes for applying a source of vacuum thereto.

2. Description of the Relevant Art

In the dental profession, dentists must remove accumulated saliva, water, and other fluids from a patient's mouth, both to keep the work area clear and to avoid the need for the dental patient to swallow such fluids. Typically, the dentist makes use of a dental saliva ejector tube, along with an associated vacuum line, for such purpose. Examples of devices proposed in the past for use by dentists in removing fluids from the patient's mouth are shown in U.S. Pat. No. 2,873,528 to Thompson, U.S. Pat. No. 3,453,735 to Burt, U.S. Pat. No. 4,083,115 to McKelvey, and U.S. Pat. No. 4,204,328 to Kutner.

In one commonly used form of dental saliva ejector tube, one end of the dental saliva ejector tube is bent to form an inverted U-shape and is inserted into the patient's mouth to aspirate collected fluids. The second, or lower end, of the dental saliva ejector tube is typically inserted into a rubber fitting or grommet secured to a vacuum line. The vacuum line may include a valve for selectively closing off the vacuum. Once the dental saliva ejector tube is inserted into the rubber fitting, the dentist may, from time to time, twist or rotate the lower end of the dental saliva ejector tube within such fitting in order to change the angle at which the upper end of the dental saliva ejector tube extends from the rubber fitting. The aforementioned dental saliva ejector tubes are currently commercially available, for example, from Spencer-Meade located in Westbury, N.Y. under the model number 951-9250; these dental saliva ejector tubes are adapted to be inserted into vacuum line sockets that are commercially available by Spencer-Meade located in Westbury, N.Y. under the model number 951-9220.

The aforementioned dental saliva ejector tubes are disposable, and a fresh dental saliva ejector tube is used for each new patient. Because they are disposable, and because a dentist may use many of such dental saliva ejector tubes each day, it is desirable that the dental saliva ejector tube itself be of relatively simple and inexpensive construction. The present inventor has noted that many dentists, dental technicians, and dental assistants experience difficulty inserting the lower end of the dental saliva ejector tube. The rubber fitting or grommet has an opening that is undersized relative to the diameter of the dental saliva ejector tube in order to form a tight seal about the lower end of the dental saliva ejector tube. In addition, the dental saliva ejector tube must be somewhat pliant, rather than rigid, so that the upper half of the tube can be bent into the aforementioned inverted U-shape. The pliancy of the dental saliva ejector tube makes it more difficult to force the lower end of the dental saliva ejector tube into the opening of the rubber fitting.

A further problem experienced by dentists is that such dental saliva ejector tubes sometimes become inadvertently dislodged from the rubber fitting or grommet, as when the vacuum line becomes temporarily snagged on an object and is pulled away from the patient's mouth. In such instances, the dental saliva ejector tube must be reinserted back into the rubber fitting, thereby interrupting the procedure in which the dentist was engaged.

Accordingly, it is an object of the present invention to provide a socket of a vacuum line for removably receiving an end of a dental saliva ejector tube which simplifies the insertion of the dental saliva ejector tube into the socket.

It is another object of the present invention to provide such a vacuum line socket which allows the dental saliva ejector tube to be easily removed therefrom when a dentist has finished working upon a dental patient.

A still further object of the present invention is to provide such a dental saliva ejector tube assembly wherein it is less likely to inadvertently dislodge the dental saliva ejector tube from the vacuum line socket.

Yet another object of the present invention is to provide such a dental saliva ejector tube assembly having the aforementioned advantages while retaining a simple and inexpensive construction.

These and other objects of the present invention will become more apparent to those of skill in the art as the description of the present invention proceeds.

SUMMARY OF THE INVENTION

Briefly described, and in accordance with the preferred embodiments thereof, the present invention relates to a vacuum line socket and dental saliva ejector tube assembly that includes a dental saliva ejector tube having a first end for being inserted into a patient's mouth and having a second end. The assembly also includes a vacuum line socket having first and second opposing ends and a central passage extending therebetween along a central axis. The first end of the vacuum line socket includes a vacuum port for being coupled to a source of a vacuum; this port is preferably barbed to form a snug fit with a vacuum hose. The second end of the vacuum line socket forms a socket for receiving the second end of the dental saliva ejector tube. Optionally, the vacuum line socket may include a valve for selectively closing the central passage extending therethrough to shut down the vacuum, as when the dental saliva ejector tube is being changed, or is not being used.

In one form of the invention, a lever is pivotally secured to the vacuum line socket. The lever includes a first end adapted to be operated by a user, and an opposing second end. Operation of the first end of the lever by the user moves the second end of the lever away from the central axis to allow the second end of the ejector tube to be inserted into, or removed from, the vacuum line socket. The second end of the lever is adapted to engage the second end of said dental saliva ejector tube, except in those instances when the user moves the first end of the lever away from the central axis. A biasing member may be used to bias the second end of the lever toward the central axis for urging the second end of the lever toward the ejector tube.

In one particular form of the invention, the second end of the lever is formed with a sharpened tip to dig into, and engage, the sidewall of the ejector tube proximate the lower end of the ejector tube. In yet another form of the invention, the lever is replaced with a slide member that slides across the vacuum line socket to selectively engage, or disengage, the sidewall of the ejector tube.

BRIEF DESCRIPTION OF THE DRAWINGS

FIG. 1 is a perspective view of a dental saliva ejector tube assembly in accordance with the present invention and including a dental saliva ejector tube and a mating vacuum line socket.

FIG. 2 is a cross-sectional drawing of the dental saliva ejector tube assembly shown in FIG. 1, in its rest position, i.e., when it is not being actuated by the user's thumb and forefinger.

FIG. 3 is a cross-sectional drawing similar to that of FIG. 2 but showing the levers of the vacuum line socket being depressed by the user's thumb and forefinger to facilitate removal of the dental saliva ejector tube from the vacuum line socket.

FIG. 4 is a top view of the vacuum line socket showing the enlarged opening of the elastic sleeve component of the vacuum line socket when the levers are actuated, as indicated in FIG. 3.

FIG. 5 is an enlarged sectional view of the lower end of the dental saliva ejector tube and illustrating an optional rib extending therefrom.

DETAILED DESCRIPTION OF THE PREFERRED EMBODIMENTS

Figure 6:
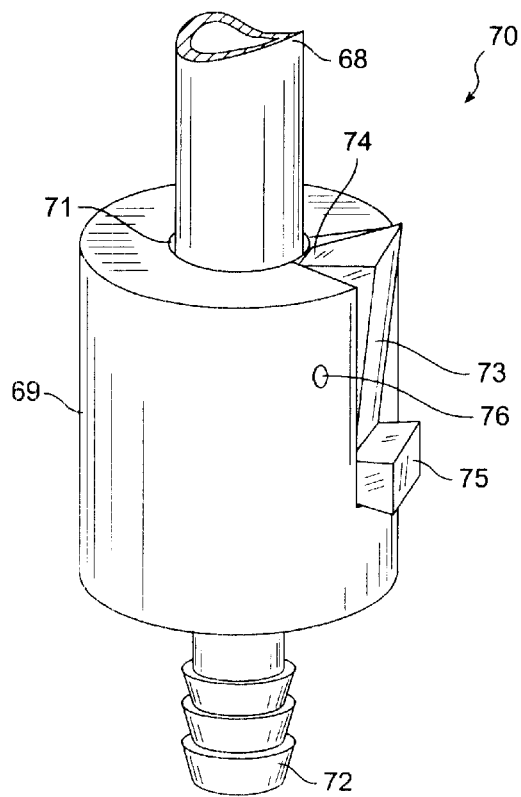
FIG. 6 is a perspective view of an alternate embodiment of the present invention wherein a lever includes an upper end having a sharp tip for engaging the side wall of the ejector tube, and a lower end for selectively moving the upper end away from the ejector tube.

A dental saliva ejector tube assembly constructed in accordance with the present invention is shown in FIG. 1, wherein reference numeral 10 generally identifies the dental saliva ejector tube and reference numeral 12 generally identifies the vacuum line socket. Ejector tube 10 is made of a pliable plastic for allowing the upper end 14 thereof to be bent into an inverted U-shape for extending over the jaw of a patient. Such ejector tubes may include a thin metal wire (not shown) embedded within the plastic and extending therealong to help keep ejector tube 10 in such bent shape, rather than returning to its original straight configuration. Upper end 14 terminates in a slotted inlet cap 16 adapted to extend within the patient's mouth; slots 18 and 20 communicate with the inner channel of ejector tube 10 and serve to suction saliva, water, and other accumulated fluids out of the patient's mouth. The lower end 22 of ejector tube 10 is circular in shape and is intended to be coupled to a source of a vacuum.

Vacuum line socket 12 is adapted to removably receive lower end 22 of dental saliva ejector tube 10. As shown best in FIGS. 2 and 3, socket 12 includes a central body 24 having a first (or lower) end 26 and a second (or upper) opposing end 28. A central passage 30 extends between first end 26 and opposing second end 28 for communicating a vacuum applied at first end 28 to second end 26. First end 26 includes a tapered port 32 for being coupled to a vacuum hose, indicated in dashed outline in FIGS. 1 and 2, which vacuum hose is coupled to a source of a vacuum and waste depository. As indicated in FIGS. 1–3, tapered port 32 may include barbs 34 for retaining tapered port 32 onto the vacuum hose. Central body 24 is preferably made of plastic or hard rubber. An optional control valve 35 (see FIG. 3) may be incorporated within central body 24 to selectively close central passage 30 and block the vacuum source from reaching opening 38; control valve 35 can be rotated manually by control knob 33 (see FIG. 1) to open or close the vacuum. Such a feature can be useful as when closing off the vacuum when the dental saliva ejector tube assembly is not in use.

The second or upper end 28 of central body 24 is in the form of a reduced diameter collar. An elastic sleeve 36, formed of pliable rubber, is secured over and around the reduced diameter collar formed at upper end 28 of central body 24 in a manner described in greater detail below. Sleeve 36 has an opening or passage 38 for receiving lower end 22 of dental saliva ejector tube 10. When at rest, in its relaxed state, the inner diameter of sleeve 36 is slightly smaller than the outer diameter of ejector tube 10 to form an airtight seal thereabout.

It will be recalled that one of the objects of the present invention is to facilitate the insertion and removal of lower end 22 of ejector tube 10 into and from socket 12. Toward such purpose, a pair of spreader members 40 and 42 are provided proximate opening 38 of sleeve 36 for enlarging opening 38 when the first and second spreader members 40 and 42 are moved apart from each other. In the preferred embodiment shown in FIGS. 1–4, first and second spreader members 40 and 42 are disposed just inside opening 38 of sleeve 36. Opening 38 is generally circular. Preferably, spreader members 40 and 42 are arcuately shaped, but the arcs thereof are defined by a somewhat larger radius than is true for the outer diameter of ejector rube 10. Accordingly, spreader members 40 and 42 tend to distort the normally circular opening 38 into a more oval shape near the upper end of sleeve 36

As shown in FIGS. 1–3, a metal bracket 46 encircles central body 24 and the lower end of sleeve 36. Bracket 46 serves to clamp the lower end of sleeve 36 about upper end 28 of central body 24. Bracket 46 may be comprised of two metal strips, each including a semicircular middle region terminating in a pair of opposing flanges or ears 48 and 50 that extend in opposing directions away from central body 24. These two metal strips extend about opposing sides of central body 24 and sleeve 36. The two strips of metal forming bracket 46 are secured to each other by hinge pins 52 and 54 which extend through the respective ears 48 and 50, respectively, to the two metal strips.

Socket 12 further includes first and second levers 44 and 56, each of which is pivotally secured by one of hinge pins 52 and 54, respectively. Thus, hinge pins 52 and 54 and bracket 46 pivotally secure each of levers 44 and 56 to central body 24. The lower ends 58 and 60 of levers 44 and 56 are twisted through an angle of ninety degrees relative to the opposing upper ends of levers 44 and 56 to provide a control surface that can be easily depressed by a user's thumb and forefinger during use.

The upper end of first lever 44 is coupled by a thin wire 62 to the first spreader member 40. Likewise, the upper end of second lever 56 is coupled by thin wire 64 to second spreader member 42. Thin wires 62 and 64 extend through small apertures formed in sleeve 36. When levers 44 and 56 are not actuated by a user, the natural elasticity of sleeve 38 pulls spreader members 40 and 42 toward each other (prior to insertion of dental saliva ejector tube 10) or against the outer walls of the dental saliva ejector tube 10 (after insertion of such dental saliva ejector tube) as shown in FIG. 2. The portions of sleeve 36 below spreader members 40 and 42 seal about the outer walls of tube 10 to form an airtight seal thereabout.

At such times that a user desires to either insert a new ejector tube 10, or to remove an existing ejector tube 10, the user grasps the lower ends 58 and 60 of levers 44 and 56 with the users thumb and forefinger, and squeezes them together in the manner indicated in FIGS. 3 and 4. This causes the upper ends of levers 44 and 56 to move apart from each other, thereby pulling spreader members 40 and 42 apart from each other, for enlarging opening 38 of sleeve 36. The enlarged opening 38 easily permits lower end 22 of ejector tube 10 to be inserted therein, or removed therefrom.

The improved socket 12 described above can be used advantageously with conventional dental saliva ejector tubes of the type already known. However, the dental saliva ejector tube 10 can be further improved by adding a generally circular rib 66 extending about the lower end 22 of saliva ejector tube 10. Rib 66 is of somewhat greater diameter than the outer wall of ejector tube 10. During insertion of lower end 22 of ejector tube 10 into opening 38 of sleeve 36, rib 66 is positioned below spreader members 40 and 42. When levers 44 and 56 are released, spreader members 40 and 42 engage rib 66 and lessen the likelihood that dental saliva ejector tube 10 can become inadvertently dislodged from socket 12. Nonetheless, rib 66 does not preclude rotation of the lower end 22 of ejector tube 10 within socket 12, as when the dentist desires to change the angle at which upper end 14 extends.

Figure 7:
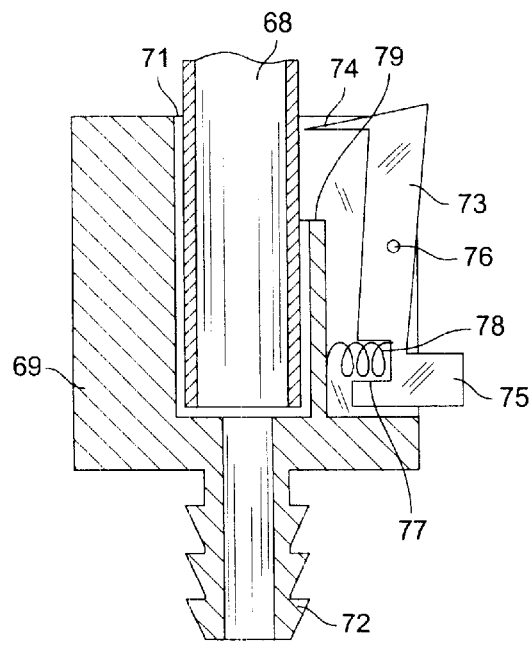
FIG. 7 is a cross-sectional view of the embodiment shown in FIG. 6.

Turning to FIGS. 6 and 7, an alternate embodiment of the present invention is illustrated. The vacuum line socket and dental saliva ejector tube assembly are designated generally by reference numeral 70 and includes dental saliva ejector tube 68 and vacuum line socket 69. The upper end of ejector tube 68 (i.e., the end which is normally inserted into a patient's mouth) is not shown in FIGS. 6 and 7. The upper end of socket 69 includes an internal central bore 71 for receiving the lower end of ejector tube 68; the lower end of socket 69 includes a barbed port 72 for being secured with a tube leading to a source of vacuum.

A lever 73 is disposed within a slot formed in the sidewall of socket 69 and includes an upper end 74 which terminates in a downwardly-directed sharpened tip and which is adapted to engage, and lightly dig into, the sidewall of ejector tube 68 near the top of socket 69. The lower end 75 of lever 73 protrudes outwardly from socket 69 for being depressed by a user. Lever 73 is pivotally secured within socket 69 by a pivot pin 76.

Referring to FIG. 7, partial wall 79 has an inner surface that engages the lower end of ejector tube 68; partial wall 79 also includes an opposing outer surface. Still referring to FIG. 7, the lower end 75 of lever 73 has a recess 77 formed therein for receiving one end of biasing spring 78; the opposite end of biasing spring 78 engages the outer surface of partial wall 79. Biasing spring 78 normally urges lower end 75 of lever 73 outward, and hence, normally urges the sharp tip of upper end 74 into engagement with the sidewall of ejector tube 68. However, if the user depresses lower end 75 of lever 73 inwardly, lever 73 rotates clockwise (relative to FIG. 7), and the upper end of lever 73 moves away from, and disengages with, ejector tube 68, thereby allowing the user to either remove an ejector tube from socket 69 or to insert an ejector tube into socket 69.

Figure 8:
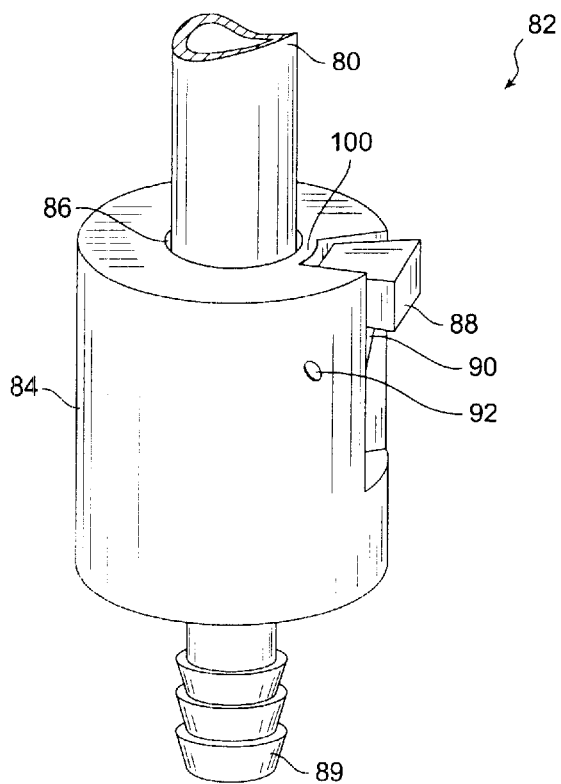
FIG. 8 is a perspective view of another embodiment of the present invention wherein a lever includes a lower end having a sharp tip for engaging the side wall of the ejector tube, and an upper end for selectively moving the lower end away from the ejector tube.
Figure 9:
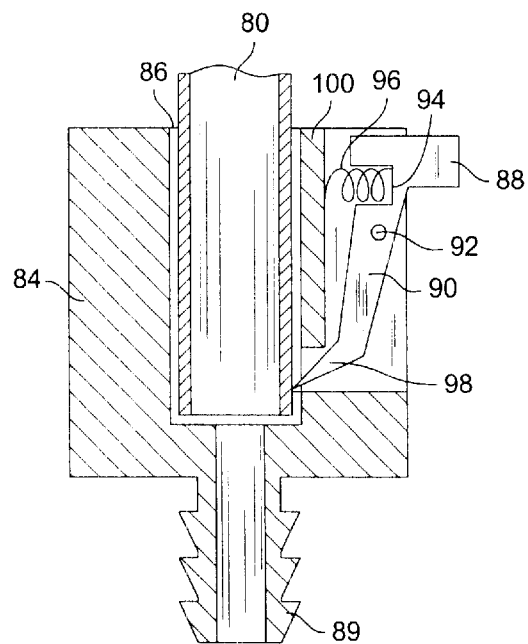
FIG. 9 is a cross-sectional view of the embodiment shown in FIG. 8.

An alternate embodiment of the invention is shown in FIGS. 8 and 9 wherein the lever described in conjunction with FIGS. 7 and 8 is instead turned upside-down. The vacuum line socket and dental saliva ejector tube assembly shown in FIGS. 8 and 9 are designated generally by reference numeral 82 and includes dental saliva ejector tube 80 and vacuum line socket 84. The upper end of ejector tube 80 (i.e., the end which is normally inserted into a patient's mouth) is not shown in FIGS. 8 and 9. The upper end of socket 84 includes an internal central bore 86 for receiving the lower end of ejector tube 80; the lower end of socket 84 includes a barbed port 89 for being secured with a tube leading to a source of vacuum.

A lever 90 is disposed within a slot formed in the sidewall of socket 84 and includes a lower end 98 which terminates in a downwardly-directed sharpened tip and which is adapted to engage, and lightly dig into, the sidewall of ejector tube 68 near the bottom of socket 84. The upper end 88 of lever 90 protrudes outwardly from socket 84 for being depressed by a user. Lever 90 is pivotally secured within socket 84 by pivot pin 92.

As shown in FIG. 9, partial wall 100 has an inner surface that engages a portion of ejector tube 80; partial wall 100 also includes an opposing outer surface. Still referring to FIG. 9, the upper end 88 of lever 90 has a recess 94 formed therein for receiving one end of biasing spring 96; the opposite end of biasing spring 96 engages the outer surface of partial wall 100. Biasing spring 96 normally urges upper end 88 of lever 90 outward, and hence, normally urges the sharp tip of lower end 98 into engagement with the sidewall of ejector tube 80. However, if the user depresses upper end 75 of lever 90 inwardly, lever 90 rotates counter-clockwise (relative to FIG. 9), and the lower end of lever 90 moves away from, and disengages with, ejector tube 80, thereby allowing the user to either remove an ejector tube from socket 84 or to insert an ejector tube into socket 84.

Figure 10:
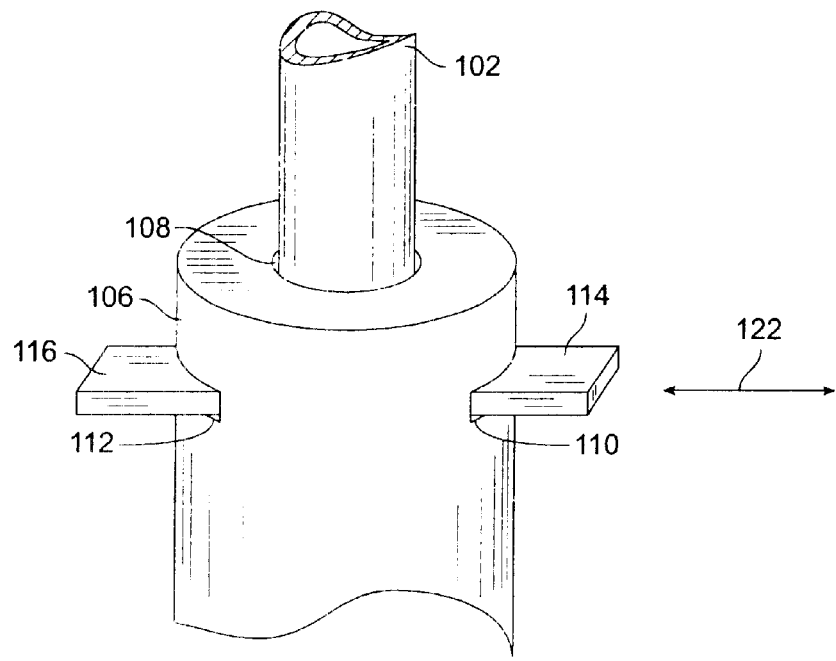
FIG. 10 is a perspective view of yet another embodiment of the present invention wherein a sliding member selectively secures the ejector tube within the vacuum line socket.
Figure 11:
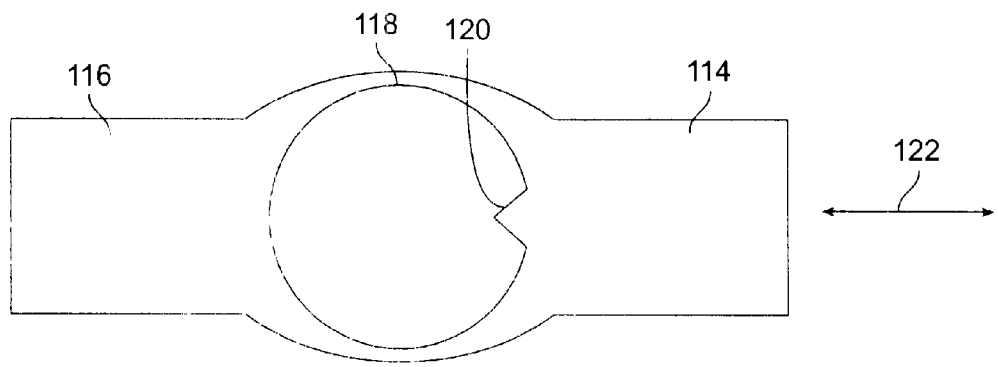
FIG. 11 is a top view of the sliding member shown in FIG. 10 and illustrating a central aperture with a sharpened tip for selectively engaging the side wall of an inserted ejector tube.

Yet another embodiment of the present invention is shown in FIGS. 10 and 11 wherein a sliding member is used instead of a pivoting lever. The vacuum line socket and dental saliva ejector tube assembly are designated generally by reference numeral 104 and includes dental saliva ejector tube 102 and vacuum line socket 106. The upper end of ejector tube 102 (i.e., the end which is normally inserted into a patient's mouth) is not shown in FIG. 10. The upper end of socket 106 includes an internal central bore 108 for receiving the lower end of ejector tube 68; the lower end of socket 106, though not shown in FIG. 10, again includes a barbed port for being secured with a tube leading to a source of vacuum.

As shown in FIG. 10, a continuous slot extends through the upper region of socket 106, terminating in opposing slotted openings 110 and 112. A slide member having opposing ends 114 and 116 extends within the continuous slot, and can slide back and forth to a limited degree in the directions indicated by arrow 122. Referring to FIG. 11, the slide member has a generally oval-shaped aperture 118 that is large enough to allow the lower end of ejector tube 102 to pass therethrough. As indicated in FIG. 11, aperture 118 includes a sharpened barb 120 which can engage, and lightly dig into, the sidewall of ejector tube 102 when end 114 of the slide member is pushed inwardly toward ejector tube 102. By making the thickness of the slide member the same as, or slightly greater than, the width of the slotted opening formed in socket 106, a friction fit is formed between the slide member and socket 106. Thus, once the user advances end 114 of the slide member inwardly toward ejector tube 102, the slide member will stay in that position until the user pushes opposing end 116 inwardly to release ejector tube 102.

Those skilled in the art will now appreciate that an improved dental saliva ejector tube assembly has been described which simplifies the insertion of the dental saliva ejector tube into the socket, and which allows the dental saliva ejector tube to be easily removed therefrom when a dentist has finished working upon a dental patient. The disclosed dental saliva ejector tube assembly can be used with conventional dental saliva ejector tubes and does not significantly increase the cost of current vacuum line sockets. While the present invention has been described with respect to preferred embodiments thereof, such description is for illustrative purposes only, and is not to be construed as limiting the scope of the invention. Various modifications and changes may be made to the described embodiments by those skilled in the art without departing from the true spirit and scope of the invention as defined by the appended claims.

I claim:

1. A vacuum line socket and dental saliva ejector tube assembly, comprising in combination:
   a. a dental saliva ejector tube having a first end for being inserted into a patient's mouth and having an opposing second end, the dental saliva ejector tube including a sidewall;
   b. a vacuum line socket having first and second opposing ends and a central passage extending therebetween, the first end including a port for being coupled to a source of a vacuum, and the second end including a central bore forming a socket for receiving the second end of the dental saliva ejector tube;
   c. a lever secured to said vacuum line socket, said lever including a first end, the first end of said lever being selectively movable toward the sidewall of said dental saliva ejector tube for retaining said dental saliva ejector tube within said vacuum line socket, and the first end of said lever being selectively movable away from the sidewall of said dental saliva ejector tube for allowing said dental saliva ejector tube to be inserted within, or released from, the second end of said vacuum line socket, the first end of said lever including a sharpened tip for selectively engaging the sidewall of said dental saliva ejector tube, said lever being pivotally secured to said vacuum line socket about a pivot axis, said lever including a second end opposite the first end thereof, wherein movement of the second end of said lever toward said dental saliva ejector tube rotates the first end of said lever away from said dental saliva ejector tube.

2. The assembly recited by claim 1 including a biasing member urging the first end of said lever toward said dental saliva ejector tube.

3. A vacuum line socket and dental saliva ejector tube assembly, comprising in combination:
   a. a dental saliva ejector tube having a first end for being inserted into a patient's mouth and having an opposing second end, the dental saliva ejector tube including a sidewall;
   b. a vacuum line socket having first and second opposing ends and a central passage extending therebetween, the first end including a port for being coupled to a source of a vacuum, and the second end including a central bore forming a socket for receiving the second end of the dental saliva ejector tube;
   c. a retaining member movably secured to said vacuum line socket, said retaining member selectively engaging the sidewall of said dental saliva ejector tube, said retaining member being capable of assuming a first position wherein said retaining member does not contact the sidewall of said dental saliva ejector tube for allowing said dental saliva ejector tube to be inserted within, or released from, said vacuum line socket, and being capable of assuming a second position wherein said retaining member does contact the sidewall of said dental saliva ejector tube for retaining said dental saliva ejector tube in said vacuum line socket, said retaining member including a sharpened tip, and wherein the sharpened tip of said retaining member does not engage the sidewall of said dental saliva ejector tube when said retaining member is in its first position, and wherein the sharpened tip of said retaining member engages the sidewall of said dental saliva ejector tube when said retaining member is in its second position.

4. The assembly recited by claim 3 wherein said retaining member is a lever pivotally secured to said vacuum line socket.

5. The assembly recited by claim 3 wherein said vacuum lines socket includes a slot extending therethrough, and wherein said retaining member is a slide member that slides through the slot extending within said vacuum line socket.

6. The assembly recited by claim 3 including a biasing member for urging said retaining member toward its second position.

7. A vacuum line socket and dental saliva ejector tube assembly, comprising in combination:
   a. a dental saliva ejector tube having a first end for being inserted into a patient's mouth and having an opposing second end, the dental saliva ejector tube including a sidewall;
   b. a vacuum line socket having first and second opposing ends and a central passage extending therebetween, the first end including a port for being coupled to a source of a vacuum, and the second end including a central bore forming a socket for receiving the second end of the dental saliva ejector tube;
   c. a lever secured to said vacuum line socket, said lever including a first end, the first end of said lever being selectively movable toward the sidewall of said dental saliva ejector tube for retaining said dental saliva ejector tube within said vacuum line socket, and the first end of said lever being selectively movable away from the sidewall of said dental saliva ejector tube for allowing said dental saliva ejector tube to be inserted within, or released from, the second end of said vacuum line socket, the first end of said lever including a sharpened tip for selectively engaging the sidewall of said dental saliva ejector tube.

8. The assembly recited by claim 7 wherein said lever is pivotally secured to said vacuum line socket about a pivot axis, said lever including a second end opposite the first end thereof, wherein movement of the second end of said lever toward said dental saliva ejector tube rotates the first end of said lever away from said dental saliva ejector tube.

9. The assembly recited by claim 8 including a biasing member urging the first end of said lever toward said dental saliva ejector tube.

* * * * *